(12) United States Patent
Kross

(10) Patent No.: US 7,678,365 B2
(45) Date of Patent: Mar. 16, 2010

(54) DISINFECTING ORAL RINSE COMPOSITIONS AND PROCESS FOR USING THE SAME

(76) Inventor: Robert D. Kross, 2506 Florin Ct., P.O. Box 374, Bellmore, NY (US) 11710

( * ) Notice: Subject to any disclaimer, the term of this patent is extended or adjusted under 35 U.S.C. 154(b) by 169 days.

(21) Appl. No.: 10/475,914

(22) PCT Filed: Apr. 27, 2001

(86) PCT No.: PCT/US01/40625

§ 371 (c)(1), (2), (4) Date: Dec. 10, 2003

(87) PCT Pub. No.: WO02/087460

PCT Pub. Date: Nov. 7, 2002

(65) Prior Publication Data

US 2004/0131557 A1    Jul. 8, 2004

(51) Int. Cl.
*A61K 8/00* (2006.01)
*A61K 8/36* (2006.01)
*A61K 8/22* (2006.01)
*C07C 59/08* (2006.01)

(52) U.S. Cl. .......................... 424/53; 424/49; 424/661; 562/400; 562/589

(58) Field of Classification Search .................. 424/49, 424/53
See application file for complete search history.

(56) References Cited

U.S. PATENT DOCUMENTS

| | | | | |
|---|---|---|---|---|
| 4,084,747 | A * | 4/1978 | Alliger | 422/20 |
| 4,902,498 | A * | 2/1990 | Agricola et al. | 424/52 |
| 5,281,412 | A * | 1/1994 | Lukacovic et al. | 424/52 |
| 5,389,679 | A * | 2/1995 | Alliger | 514/557 |
| 5,622,725 | A | 4/1997 | Kross | |
| 5,667,817 | A | 9/1997 | Kross | |
| 5,738,840 | A | 4/1998 | Richter | |
| 5,772,986 | A | 6/1998 | Kross | |
| 5,820,822 | A * | 10/1998 | Kross | 422/37 |
| RE36,064 | E * | 1/1999 | Davidson et al. | 424/665 |
| 6,039,934 | A | 3/2000 | Alliger | |
| 6,235,269 | B1 | 5/2001 | Witt et al. | |

* cited by examiner

*Primary Examiner*—Frederick Krass
*Assistant Examiner*—Lezah W Roberts
(74) *Attorney, Agent, or Firm*—Henry D. Coleman; R. Neil Sudol; William J. Sapone

(57) ABSTRACT

This invention relates generally to compositions and methods useful for oral hygiene rinses, and more specifically to oral rinses in which the antimicrobial activity of chlorous acid is supplemented by that of lactic acid as one of a combination of antimicrobial acids, preferably acids which serve to partially convert chlorite ion to chlorous acid.

14 Claims, No Drawings

DISINFECTING ORAL RINSE COMPOSITIONS AND PROCESS FOR USING THE SAME

TECHNICAL FIELD

This invention relates generally to compositions and methods useful for oral hygiene rinses, and more specifically to oral rinses in which the antimicrobial activity of chlorous acid is supplemented by that of lactic acid as one of a combination of antimicrobial acids, preferably organic acids, which serve to partially convert chlorite ion to chlorous acid.

BACKGROUND OF THE INVENTION

In the last few decades a large number of antimicrobial systems have been developed that are based on the in-situ creation of metastable chlorous acid, under conditions where the chlorous acid, $HClO_2$, represents a relatively small fraction of the total aqueous chlorite ($ClO_2^-$). The antimicrobially-effective chlorous acid systems function at pH values from about 3.5 down to about 2.5. The protic acid source to effect this conversion is generally an organic acid. These acidified chlorite compositions were first taught by Alliger in 1978 (U.S. Pat. No. 4,084,74) and in 1982 (U.S. Pat. No. 4,330,531), as germ-killing compositions with a broad-range of high activity against bacteria, fungi and viruses. In Alliger's compositions the acid activator, lactic acid, was deemed to be critical, and the quantity of lactic acid utilized had to represent at least about 15% by weight of the total amount of organic and inorganic acids present. Subsequently Tice, in 1986 (U.S. Pat. No. 4,585,482), disclosed long-active biocidal compositions in which sodium chlorite is slowly activated by the slow degradation of acid-generating polymers, such as poly(lactic acid). Several patents followed thereafter in which lactic acid, among other protic acids, was used in combination with chlorite salts for the purpose of skin disinfection, specifically as components of barrier formulations (U.S. Pat. No. 4,891,216), a genital herpes treatment (U.S. Pat. No. 4,956,184), or in anti-inflammatory formulations (U.S. Pat. No. 5,384,134).

Subsequent prior art taught the creation of a diverse range of chlorous acid compositions and their method of use. All but one (U.S. Pat. No. 5,820,822) were based on the use of protic acids, primarily organic acids, to transform chlorite to chlorous acid. These organic acids did not include lactic acid, as a result of Alliger's earlier disclosure of lactic/chlorite disinfection systems, wherein lactic acid was required to be at least 15% by weight of all acids present. These subsequent art disclosures are embodied in U.S. Pat. Nos. 4,986,990 (1991), U.S. Pat. No. 5,185,161 (1993) and RE36,064 (1999), all issued to Davidson and Kross. A process for using chlorous acid solutions to remove bacteria from poultry and other meats, issued to Kross (U.S. Pat. No. 5,389,390), included lactic acid as a prospective acidifying agent for the chlorite, but it was also disclosed that technical-grade lactic acid was inappropriate for such use because impurities in commercial sources of lactic acid caused the unwanted generation of chlorine dioxide ($ClO_2$), and this was found to cause undesirable discoloration and bleaching of poultry skin This inventor has also noted that $ClO_2$ causes similar, undesirable staining of protein deposits in soft contact lenses, following repeated use of the lenses and their subsequent disinfection in a $ClO_2$ solution. The discoloration is most probably ascribable to the oxidative transformation, by $ClO_2$, of labile amino acids (specifically tyrosine and tryptophan) in common proteins, to form colored materials (see Masschelein).

In the patent issued to Kross et al. (U.S. Pat. No. 5,100,652) "Disinfecting Oral Hygiene Compositions and Process for Using the Same," which was based on chlorite solutions activated by an organic acid, lactic acid was specifically excluded from the list of organic acids that might be used in such solutions. Although this exclusion was necessary because of the earlier teachings of Alliger, lactic acid at that point was deemed to be an inappropriate mouth rinse acidifier, owing to its particularly undesirable sour taste. Thus its exclusion was not considered as limiting, when formulating effective, commercializable antimicrobial oral formulations. In the practice of the technology disclosed in Kross' oral hygiene U.S. Pat. No. 5,100,652, this same inventor has since learned that formulations which contain glycerin, particularly at levels above about 10% in the mixed composition, result in unacceptable staining of users' teeth. The use of such compounds, which contain vicinal hydroxy groups, were taught in that patent to be a means of releasing chlorine dioxide into the oral rinse for additional germicidal benefit. Nevertheless the adverse discoloration of teeth is now recognized to derive from chlorine dioxide, whether generated by glycerin-like compounds or the impurities associated with technical-grade lactic acid. At lower levels of $ClO_2$ in oral rinse compositions the adverse staining effects take longer to notice, but for rinse products which are used twice-daily, for months and years, the increasing discoloration would dissuade consumers from further use. Thus the inappropriate taste of lactic acid as well as the propensity of normal, commercial lactic acid to cause unwanted tooth staining, would seem to argue strongly against its potential inclusion in oral rinse formulations.

Subsequent oral compositions based on acidified chlorite systems are those taught by Lukacovic et al. (U.S. Pat. No. 5,281,412), in which acidified chlorite solutions require a citrate ion source to reduce staining, and Witt et al. (U.S. Pat. Nos. 6,077,502 and 6,132,702) where the chlorite solutions are above pH 7, and contain effectively no $ClO_2$ or chlorous acid.

Continued experiments intended to optimize the efficacy of oral rinse solutions has led this inventor to review and reconsider the potential contribution of lactic acid to these systems. This need was based on the fact that chlorous acid oral rinse systems are short lived, and subject to loss of activity upon salivary dilution and the resultant pH rise, while many organic acids will maintain some level of germ-killing activity in solutions with $H^+$ concentrations one-tenth or less of their initial level in the chlorous acid oral rinse. The re-investigation of lactic acid specifically was driven by the fact that lactic acid is the most effective antimicrobial acid among those listed by the US Food & Drug Administration as Generally Recognized As Safe (GRAS) as food acidulants. The GRAS designation is accorded to materials which possess the highest recognized safety for food use; and GRAS acids, therefore, are the most appropriate to use for potentially-ingestible oral hygiene compositions. It is well recognized that lactic acid is more effective, for example, than malic, citric, tartaric, succinic, adipic, and fumaric acids, which are all GRAS acids. Among these acids, other than lactic, malic acid is the most active germicide, but when compared with lactic acid, it is significantly less effective. When lactic acid was compared with malic acid, on the basis of equimolar amounts of the unionized acid form, using an AOAC [Association of Official Analytical Chemists] Germicidal Test procedure, malic acid destroyed 1.45 $logs_{10}$/ml organisms of an initial inoculum of E. coli of 7.63 $logs_{10}$/ml, whereas lactic acid killed 4.15 $logs_{10}$/ml of the same population. Numerically, after disinfection, there were ~1500 times more residual *E. coli* organisms, per ml of solution, in the malic acid-treated suspension as there were in the lactic-acid treated suspension.

As already indicated, the impediments to the use of lactic acid in an oral rinse are its unpleasant taste and its tendency to trigger undesirable $ClO_2$ formation in chlorite solutions, when included as the technical-grade material. The latter is generally ~88% pure, and is the only form available commercially in appropriate bulk quantity, at a cost less that $1 per lb. This is in contrast to the limited quantities of "pure" (98%) lactic acid available from specialty chemical houses, at 10-times that price.

This invention is the result of efforts to capitalize on the well-recognized antimicrobial activity of lactic acid, as an auxiliary cidal agent to that of chlorous acid, while overcoming the limitations imposed by lactic acid's unpleasant taste as well as the $ClO_2$-generating impurity effects of "technical-grade" lactic acid, the common commercial commodity. I have discovered that there is a unique "window" between the "0", proscribed use level for lactic acid as the sole organic acid activator for chlorite in the Kross (U.S. Pat. No. 5,100,652) "Disinfecting Oral Hygiene Compositions. . . " disclosure, and Alliger's teaching that lactic acid must represent at least 15% by weight of the acid(s) required to activate chlorite in his disinfecting compositions. I have found that the high germicidal potency of lactic acid allows for its effective use at levels low enough to avoid unpleasant tastes, and particularly, when included in the compositions in the manner taught in the following disclosure, effectively overcomes the staining potential engendered by $ClO_2$-triggering impurities in technical-grade lactic acid. The lactic acid use level, in combination with at least one other organic acid activator, satisfies all of the technical and organoleptic requirements listed above, while uniquely fitting into the 0 to <15% concentration range window stipulated in the prior art.

OBJECTS OF THE INVENTION

It is, therefore, an object of the present invention to provide a composition and a process for the use of lactic acid to enhance and prolong the antimicrobial capabilities of acidified-chlorite oral hygiene formulations.

It is a further object of this invention to achieve a level of use of lactic acid in these oral rinses, in combination with at least one other organic acid activator, such that the resulting taste of the oral composition is not adversely impacted by the unpleasant flavor of lactic acid.

It is yet a further object of this invention to include lactic acid in the acid-activator component of acidified-chlorite oral rinses in a manner so as to minimize the formation of chlorine dioxide, and thereby avoid undesirable teeth staining.

And it is yet a further object of this invention to achieve the previous objects by employing lactic acid in these acid-chlorite rinses at levels which have not been previously taught.

These, and/or other objects of the present invention may be readily gleaned from a detailed review of the description of the invention which follows:

SUMMARY OF THE INVENTION

The present invention relates to the discovery that low levels of lactic acid in two-part acid-chlorite oral hygiene compositions, specifically between about 2% of the total weight of the acid activators and less than about 12% by weight of the acid activators of the chlorite found in the final composition, can enhance the germicidal qualities of such compositions. Specifically this range of levels circumvents the adverse negative taste that would be imparted to acid-chlorite oral compositions were lactic acid to be used either alone as the acid activator, or at levels greater than about 15% by weight of combined acids present. The antimicrobial benefit of the lactic acid, even at these prescribed use levels, results from its significantly greater germicidal efficacy than that of any other available acid, such availability being based on the acknowledged safety of such acids in orally-ingested products, as well as the palatability of the acid.

It has been further discovered that the adverse tooth staining qualities engendered by the use of commonly-available lactic acid in such oral rinse compositions, based on the impurities in the technical-grade product, can be overcome through the in-situ creation of lactic acid in the acid-part from its corresponding metal salt (preferably, water soluble and more preferably the sodium or potassium salt of lactate), by appropriate addition to that part of an equivalent amount of a stronger acid (i.e., having a $pK_a$ which is lower than that of lactic acid at 3.86), either inorganic (e.g., mineral acid) or organic, or a weaker acid which has been included in sufficient excess to the lactic acid to create the lactic acid. The amount of metal lactate salt selected for use is such that the level of lactic acid created therefrom is in the above-specified 2% to 12% (i.e., about 2% to about 12% by weight of the acids used in the composition) relative weight range.

In one aspect of this invention, the lactate salt is calcium lactate which, upon acidification to liberate free lactic acid, provides calcium ions to the composition, of benefit in suppressing demineralization of tooth enamel. In another aspect the lactate salt is sodium lactate, which use is favored when fluoride ion is included in the composition.

The pH of the oral rinse system comprised of lactic acid and at least one other acid, and a metal chlorite salt, will generally lie in the range of about 2.5 and about 3.5, the specific value thereof being dependent upon the nature and quantity of the acids present and, to a lesser extent, the quantity of metal chlorite salt used in the mixed composition. The amount of metal chlorite in the composition ranges preferably from about 0.05% to about 0.5% based on the total weight of the composition. Other agents may be used in these compositions to impart such other desired qualities as color (coloring agents), flavor (flavoring agents), aroma (aromatic agents), texture (texturizing agents), surfactancy (surfactants, emulsifiers), and suppressed tooth demineralization. These well-known components may be added in effective amounts to compounds according to the present invention.

Methods of using compositions according to the present invention in oral hygiene formulations to reduce microbial growth in the mouth a mammal are other aspects of the present invention. In this method, a composition according to the present invention is used as an oral hygiene rinse in the mouth of a mammal, preferably a human, for a period sufficient (generally, at least about 5-10 seconds and upwards of several minutes or more) to reduce microbial growth in the mouth of the mammal.

DETAILED DESCRIPTION OF THE PRESENT INVENTION

The term "chlorite" or "chlorite salt" is used throughout the specification to describe a salt of chlorite which is readily soluble in an aqueous system and which readily dissociates into chlorite anion and counterion (generally, metal). Two particularly preferred salts of chlorites for use in the present invention include sodium chlorite and potassium chlorite.

The term "acid" or "acid activator" is used throughout the specification to describe protic acids, i.e., acids that release hydrogen ions in solution, which may be combined with lactic acid to produce compositions according to the present invention. Acids for use in the present invention may include inorganic acids such as hydrochloric, sulfuric and nitric acid, benzenesulfonic acid, among other organic sulfonic acids, but preferably, include organic acids such as acetic, benzoic, citric, fumaric, glycolic, malic, maleic, tartaric acid, citric, propionic, acetic, succinic, adipic, and mandelic, among others, including ethylenediaminetetraacetic acid (EDTA, as the free acid or the monosodium salt), among numerous others. It is noted that numerous additional acids may also be used in the present invention. In its broadest aspect, compositions according to the present invention may make use of virtually any orally compatible acid in combination with lactic acid, to the extent that it provides an initial pH, which when the chlorite-containing part and the acid-containing part are combined to produce an initial pH preferably ranging from about 2.5 and about 3.5. One of ordinary skill will be able to readily determine the type and amount of acid to be used for a particular application.

The term "effective" is used to describe concentrations of amounts of individual components according to the present invention which are included in compositions in order to produce an intended effect. In the case of the use of the term "effective" with respect to the time of an application, such definition is that amount of time which is used to produce an intended result, for example, the decrease in numbers or growth of microbial flora within the mouth.

The oral hygiene rinse compositions of this invention comprise aqueous solutions containing a suitable amount of two or more carboxylic acids, one acid of which is lactic acid such that its total amount is not greater than about 12% of the total weight of such acids, a suitable amount of a metal chlorite at a pH adjusted to favor its stability, and one or more flavoring agents. The compositions are prepared for use directly prior to oral intake, generally by combination of equal volumes of two aqueous parts. One part is comprised of the acids and flavor; the other part is comprised of the metal chlorite. Typically the amount of combined acids is sufficient to reduce the pH of the mixed oral rinse to between about 3.5 and about 2.5. The amount of metal chlorite in the mixed oral rinse is typically in the range of about 0.05% to about 0.5%.

In a preferred embodiment the lactic acid is prepared in situ by stoichiometric combination of a lactate salt and a strong inorganic acid other than phosphoric acid, or by combination of a lactate salt and another carboxylic acid of an acid strength greater than that of lactic acid, such that the calculated degree of conversion of the lactate to lactic acid is at least 70% (i.e. the calculated molar ratio of lactic acid to lactate ion is at least 2.3). In certain embodiments of this invention the carboxylic acids that are used in combination with the lactic acid are those accorded the GRAS status by the FDA, so that the partial ingestion of the oral hygiene rinse during use, which occurs to about the 10% level, will cause no untoward toxicological effects. The list of GRAS carboxylic acids, besides lactic acid, includes malic, citric, tartaric, succinic, adipic, and fumaric acids. Benzoic acid is also a GRAS acid, and its presence in the inventive composition will also supplement the antimicrobial qualities of the acid-chlorite composition Among these embodiments, malic acid is a preferred acidifier for the chlorite salt, since its immediate perceived taste sensation is less than most of the other carboxylic acids, such as citric, which promotes a very rapid sour burst in the mouth. Another embodiment includes the non-GRAS acid, mandelic acid, which has significant germicidal properties, but an oral rinse formulation containing this acid would require significant toxicological testing to validate its safety.

The level of about 12% lactic acid by weight of total carboxylic acid in the composition, represents an apparent threshold, above which the flavor of lactic acid per se becomes perceptible as compared with that of a composition prepared without it, using the same other carboxylic acid. This is a variable figure, depending to a significant degree on the sensitivity of the user and the flavor characteristics of the other acid. When citric acid is used as the supplemental acid, less total acid is required to achieve a desired pH than, say, when using malic acid, which is half the strength of citric ($K_{a1}$ of citric is $8.2 \times 10^{-4}$ vs. $3.9 \times 10^{-4}$ for malic acid). Thus a smaller amount of lactic acid is used when it represents, say, 10% of a lactic/citric combination than a lactic/malic combination; but the tart taste of citric, reduced by its relatively lower level, can be similarly intruded upon by that of the lactic. Thus it is important, in practicing this invention, to conduct taste-evaluations of candidate carboxylic acids other than lactic acid alone, to determine the proper level for a desired pH, prior to supplementation with lactic acid to levels from about 2% to about 12% of the total weight of the combined acids.

In certain embodiments, the metal lactate in these compositions is an alkali, an alkaline earth lactate, or a heavier metal lactate. The alkali metal lactate class includes the lactic acid salts of sodium, potassium and ammonium, of which sodium lactate is the preferred source of regenerated acid. Useful alkaline earth metal lactates include magnesium and calcium lactate. Available heavier metal lactates are ferrous and aluminum lactates, although the cation flavor is intrusive. The amount of metal lactate salt selected for use is such that the level of lactic acid created therefrom is in the above-specified 2% to 12% relative weight range. It has been found generally that at the stronger end of the inventive pH range, between about 2.5 and about 3.0, the level of metal lactate required for suitable germicidal efficacy is at the lower end of the inventive range, i.e. from about 0.05% to about 0.25% in the mixed composition. At pH values between about 3.0 and about 3.5, metal lactate levels between about 0.25% and about 0.5% are needed for comparable efficacy of the chlorous acid system. Factoring into these considerations is the fact that the germicidal enhancement provided by the lactic acid depends on the relative amount of the free acid form (the active cidal species) with respect to that of the lactate ion. At pH 2.5 96% of the two lactic species exist as lactic acid, which drops to 70% at pH 3.5. At higher pH values, the reduced amount of the intact lactic acid molecule (e.g. 42% of total, at pH 4.0) no longer warrants its inclusion as a germicidal enhancer.

The lactic acid can be included in the acid activator portion, from about the 2% to about the 12% level with respect to the weight of the multiple acids in the activator, using either the intact acid or as a lactate salt which is converted, during preparation, to the whole acid form. The intact acid is currently available, on an economic basis, as the technical grade liquid material with a degree of purity approximating 88%. When that material is employed, it is necessary to determine its percent purity by such standard procedures as the back-titration method provided in the United States Pharmacopeia. When using the metal lactate salt, the desired weight of final acid must be determined by calculation, so as to lie within the stipulated 2% to about 12% range as percentage of total activating acids. For example, to achieve a specific percentage level of lactic acid with respect to the total weight of the activating acids, it is necessary to first determine the actual weight of lactic acid that is desired to be in the acid composition, and then multiply by the relative molecular weights of the metal salt and lactic acid. For sodium lactate, the multiplication factor would be 112.07÷90.08, or 1.244. For a multivalent lactate salt, its molecular weight should be divided the metal's valence. Corrections for lactate impurities should also be made, as for example dividing the calculated weight of sodium lactate by the fractional concentration in the commercially-available solution form, usually of 70%-80% purity.

Other materials may be incorporated into either of the two parts of the inventive compositions, so as to improve the stability of each part, as well as improve and/or enhance the organoleptic qualities, the safety, and the efficacy of the mixed acidified chlorite composition. The stability of the aqueous chlorite phase is generally favored by pH values over about 8.5, preferably over 9.2, and most preferably over 10.0. Adjustment of pH can be accomplished by use of standard alkaline materials known to those skilled in the art, such as sodium or potassium hydroxide. Additional components which have value in certain embodiments include surface active agents, colorants, humectants, flavorants, sweeteners, fluoride ion sources, calcium sources and thickeners. Appropriate members of these classes are known to experienced oral rinse formulators, and need not be specifically identified herein. Levels of use of these materials are typically the following, expressed on the mixed formulation basis: Surface active agents (about 0.05% to about 5.0%), humectants (from about 0% to about 25%, with care taken that the level of humectant selected causes no undue triggering of chlorine dioxide formation from acidified chlorite), flavoring agents (from about 0.04% to about 2.0%), sweeteners (artificial and natural) (from about 0.02% to about 3.0%), and coloring agents (from about 0.0001% to about 0.2%).

Preferred compositions include fluoride ion, to suppress enamel demineralization and caries formation in teeth. Typical fluoride ion levels are from about 0.02% to about 0.30% of the final composition, derived from fluoride sources such as sodium fluoride, stannous fluoride, indium fluoride and sodium monofluorophosphate. Thickeners have the advantage of extending the presence of the rinse in the oral cavity, by virtue of the attendant resistance to salivary dilution. They are typically used at levels from about 0% to about 5% in these inventive compositions. In a preferred composition xanthan gum has been found to offer the advantage of stability in both the acid activator and the chlorite phases. Generally the colorants and flavorants are selected to be both aesthetically appealing and of sufficient stability, in both the part in which they are included and in the mixed composition, which is an oxidizing environment.

The following non-limiting examples further describe preferred embodiments within the scope of the present invention. Many variations of these examples are possible without departing from the spirit of the invention.

EXAMPLE 1

This examples demonstrates the tendency for lactic acid, technical grade, to cause unwanted amounts of chlorine dioxide in an oral rinse solution, as compared with an equivalent-strength malic acid activating solution, when combined with identical chlorite solutions. Based on the relative acid ionization constants for lactic and malic acids, i.e. $1.38 \times 10^{-4}$ and $3.9 \times 10^{-4}$, resp., equal volumes of 2.39% technical-grade (88%) lactic acid and 0.75% malic acid (pure) were combined 1:1 with 0.32% (pure basis) sodium chlorite solutions that had been adjusted to a pH ~10.5. The acid and chlorite solutions had first been equilibrated at 37° C., to simulate body temperature. The solution pHs, in both cases, were 3.0. After 10 minutes, the solution Absorbance values were measured at a wavelength of 360 nM in a spectrophotometer, and the concentration of chlorine dioxide ($ClO_2$) then calculated, using the molar extinction coefficient of 1,242 liter/mole.cm. A concentration of 7.1 ppm of $ClO_2$ was found in the lactic acid/chlorite oral rinse solution, and <1 ppm $ClO_2$ in the malic acid/chlorite rinse solution.

The rapid generation of $ClO_2$, with its tooth-staining potential, particularly after repeated daily use, clearly minimizes the value of oral rinse solutions containing the significant levels of $ClO_2$ associated with the use of technical-grade lactic acid as the sole chlorite activator.

EXAMPLE 2

This example shows the protein-staining caused by the $ClO_2$ generated in the lactic/chlorite solution prepared in Example 1, as compared with that from the malic/chlorite oral rinse, 1 ml of freshly-isolated liquid egg albumen was added to 5 ml of each of the two rinse solutions and a malic/water control. The albumen protein in the lactic/chlorite solution turned pink immediately, while there was no discoloration noted in either the malic acid solution or the control. This demonstrates how $ClO_2$, as triggered by the lactic acid impurities, will cause demonstrable staining of the proteins commonly found on tooth surfaces, particularly the pellicle and bacterial plaque.

EXAMPLE 3

This example demonstrates how technical-grade lactic acid may be used in combination with another organic acid, as a mixed activator of a chlorite solution, so that no perceptible increase of $ClO_2$ is found to occur in the solution, as compared with a one-part acid activator with the other, non-lactic acid. A mixture was prepared with 0.75% malic acid and 0.116% technical-grade lactic acid, containing 0.102% pure lactic acid, wherein lactic acid represented 12.0% by weight of the total acids in the activator. An activator containing malic acid alone was prepared, containing 0.786% malic acid [0.75%+0.036%; i.e. the malic equivalent of the 0.116% lactic acid]. These solutions, after equilibration at 37° C., were mixed in equal volumes with similarly-equilibrated solutions containing 0.32% sodium chlorite, on a pure basis, having a pH of 10.5. Upon mixture, both oral rinses had pHs of 2.96. Spectrophotometric analysis of the two solutions, as in Example 1, indicated that less than 1 ppm of $ClO_2$ was generated after 10 minutes. When 1 ml of fresh albumen was added to 5 ml aliquots of each of the two oral rinse solutions, as in Example 2, no pink color developed in either tube, indicating a minimum tendency to discolor protein.

EXAMPLE 4

This example demonstrates that lactic acid can be prepared from a lactate metal salt, and used in combination with a metal chlorite solution, as in Example 1, without creation of significant quantities of $ClO_2$. A portion of calcium lactate was dried in a 105° C. oven, and a sufficient quantity of the desiccated powder was added to water to make a 2.54% aqueous solution. Prior to final dilution, a stoichiometric amount of hydrochloric acid (4.7 ml of 5.0N) was added to the solution to convert the calcium lactate to free lactic acid, to the degree that obtains at the pH of the acid solution. Upon combination of that solution, equilibrated to 37° C., with an equal volume of a 0.32% sodium chlorite solution, at pH 10.5 and at 37° C., the solution was allowed to stand 10 minutes and its Absorbance at 360 nM was measured spectrophotometrically. The reading corresponded to a $ClO_2$ level of <1 ppm, as compared with the 7.1 ppm found in Example 1 when a comparable amount of technical-grade, free lactic acid was utilized. Addition of 1 ml of fresh egg albumen to 5 ml of the lactate-derived oral rinse resulted in no discoloration of the protein, which confirms that the absence of significant $ClO_2$ levels minimizes the potential staining problem.

However, the taste of the lactate-derived oral rinse was highly objectionable, and corresponded to the sour, off-taste of the lactic acid rinse of Example 1. Thus the use of lactic acid as the single acid activator of a metal chlorite, to serve as an acceptable oral hygiene rinse, is not at all feasible.

EXAMPLE 5

This example is a counterpart of Example 3, with the exception that the 12.0% lactic acid by weight of the mixed acid was herein created by acidification of calcium lactate, thereby avoiding the introduction of $ClO_2$-generating lactic acid impurities. Specifically, 0.1235 gms of anhydrous calcium lactate was added to 0.75 gms of malic acid (pure), which was dissolved in sufficient water to bring the total volume to 100 ml after the addition of 1.13 ml of 1N hydrochloric acid. The latter was sufficient to convert the lactate ion to lactic acid, to the degree that occurs at the pH of the acid mix. This solution, after equilibration at 37° C., was mixed with an equal volume of a similarly-equilibrated solution containing 0.32% of sodium chlorite, on a pure basis, having a pH of 10.5. Upon mixture, the oral rinse had a pH of 2.98. The taste of the product was acceptable as an oral rinse, even though it had no excipients to improve its organoleptic qualities, e.g. flavor, sweetener, color.

EXAMPLE 6

This example provides a more-acceptable, commercializable oral hygiene product that contains appropriate excipients for both aesthetic appeal and improved functionality, as compared with a corresponding oral rinse lacking the specified ingredients. The acid activator solution of Example 5 is prepared by first addition of 0.05% sodium benzoate to the bulk of the water, followed by 0.05% sodium saccharin, and 0.20% of xanthan gum with subsequent mixing. After dispersal of the latter, the calcium lactate and malic acid are added, in the amounts specified, followed by 0.0002% of FD&C Blue #1. After the gum has fully hydrated, an amount of 1N hydrochloric acid is then carefully and slowly added to reduce the solution pH to 2.8-2.9. The water volume is brought to ~95% of the required volume, and then an amount of L-menthol crystals are dissolved in the mixture with continuous stirring. Upon complete dissolution, the volume is increased to the final desired value.

The chlorite phase of the oral hygiene product is prepared from a fresh dispersion of 0.2% xanthan gum, to which is added an amount of sodium chlorite, based on its degree of purity, sufficient to form a 0.32% aqueous solution. To that solution is added enough sodium fluoride to make a 0.08% solution, and a quantity of alkali needed to bring the solution pH to the pH 10.5-10.8 range.

The admixture of equal volumes of the acid activator solution and the chlorite solution provides an antimicrobial oral rinse that is organoleptically acceptable, causes no tooth staining, and combines immediate germicidal activity from the chlorous acid system with the extended antimicrobial action provided by lactic acid. The slight thickening of the formula, with xanthan gum, is of benefit to both germicidal components, since it suppresses the dilution of the rinse by saliva, and thereby prolongs the life of the chlorous acid system and the level of lactic acid with respect to its lactate ion counterpart.

References Cited
U.S. Patent Documents

| Number | Issue Date | Inventor | U.S. Class |
|---|---|---|---|
| 4,084,747 | April, 1978 | Alliger | 239/4 |
| 4,330,531 | May, 1982 | Alliger | 424/149 |
| 4,585,482 | April, 1986 | Tice et al. | 106/15 |
| 4,891,216 | January, 1990 | Kross et al. | 424/78 |
| 4,986,990 | January, 1991 | Davidson et al. | 424/665 |
| 5,100,652 | May, 1992 | Kross et al. | 424/53 |
| 5,185,161 | February, 1993 | Davidson et al. | 424/665 |
| 5,384,134 | January, 1995 | Kross et al. | 424/661 |
| 5,389,390 | February, 1995 | Kross | 426/332 |
| 5,597,561 | January, 1997 | Kross | 424/78 |
| 5,628,959 | May, 1997 | Kross | 422/37 |
| 5,651,977 | July, 1997 | Kross | 424/419 |
| 5,772,985 | June, 1998 | Kemp et al. | 424/45 |
| 5,820,822 | October, 1998 | Kross | 422/37 |
| RE36,064 | January, 1999 | Davidson et al. | 424/665 |
| 6,063,425 | May, 2000 | Kross | 426/335 |
| 6,077,502 | June, 2000 | Witt et al. | 424/53 |
| 6,096,350 | August, 2000 | Kemp et al. | 424/661 |
| 6,132,702 | October, 2000 | Witt et al. | 424/53 |

OTHER REFERENCES

Masschelein, W J; (1979) *Chlorine Dioxide; Chemistry and Environmental Impact of Oxychlorine Compounds*. Ann Arbor Science, Mich.

I claim:

1. A palatable antimicrobial oral hygiene rinse composition comprising water and a chlorite salt in combination with an acid combination comprising lactic acid and at least one additional protic acid, said acid combination producing in combination with said chlorite salt an in situ effective amount of chlorous acid in said rinse composition at a pH ranging from about 2.5 to 3.5, said lactic acid comprising 2% to 12% by weight of said acid combination, wherein said additional acid is selected from the group consisting of citric, fumaric, glycolic, malic, tartaric acid, succinic, adipic, mandelic, and mixtures thereof.

2. The composition according to claim 1 wherein said chlorite salt ranges from about 0.05% to about 0.5% by weight of said composition.

3. The composition according to claim 1 wherein said chlorite salt is sodium chlorite or potassium chlorite.

4. The composition according to claim 1 wherein said lactic acid is prepared in situ by the stoichiometric combination of a lactate salt and a protic acid having a $pK_a$ of less than lactic acid and/or an excess of a protic acid which has a $pK_a$ which is greater than lactic acid.

5. The composition according to claim 1 wherein said composition further comprises at least one additive agent selected from the group consisting of surface active agents, colorants, humectants, flavorants, sweeteners, fluoride ion sources, calcium sources and thickeners.

6. A method of reducing the number of microorganisms in the mouth cavity of a mammal, said method comprising exposing said mouth cavity to a composition according to claim 1 for a period of time effective to reduce the number of microorganisms in said mouth cavity.

7. A method of reducing the number of microorganisms in the mouth cavity of a mammal, said method comprising exposing said mouth cavity to a composition according to claim 2 for a period of time effective to reduce the number of microorganisms in said mouth cavity wherein said composition comprises a fluoride ion source or a calcium source.

8. A method of reducing the number of microorganisms in the mouth cavity of a mammal, said method comprising exposing said mouth cavity to a composition according to claim 2 for a period of time effective to reduce the number of microorganisms in said mouth cavity.

9. A method of reducing the number of microorganisms in the mouth cavity of a mammal, said method comprising exposing said mouth cavity to a composition according to claim 3 for a period of time effective to reduce the number of microorganisms in said mouth cavity.

10. A method of reducing the number of microorganisms in the mouth cavity of a mammal, said method comprising exposing said mouth cavity to a composition according to claim 4 for a period of time effective to reduce the number of microorganisms in said mouth cavity.

11. A method of reducing the number of microorganisms in the mouth cavity of a mammal, said method comprising exposing said mouth cavity to a composition according to claim 5 for a period of time effective to reduce the number of microorganisms in said mouth cavity.

12. A method of reducing the number of microorganisms in the mouth cavity of a mammal, said method comprising exposing said mouth cavity to a composition according to claim 5 wherein said composition comprises a fluoride ion source or a calcium source for a period of time effective to reduce the number of microorganisms in said mouth cavity.

13. The composition according to claim 1 wherein said acid is an α-hydroxy acid selected from the group consisting of citric, glycolic, malic, tartaric, mandelic and mixtures thereof.

14. A method of reducing the number of microorganisms in the mouth cavity of a mammal, said method comprising exposing said mouth cavity to a composition according to claim 13 for a period of time effective to reduce the number of microorganisms in said mouth cavity.

* * * * *